United States Patent
Vanzuilen et al.

(10) Patent No.: US 6,927,583 B2
(45) Date of Patent: Aug. 9, 2005

(54) FUEL SENSOR

(75) Inventors: David M. Vanzuilen, Fremont, IN (US); Gerard Mouaici, Toulouse (FR); Francois-Xavier Bernard, Corronsac (FR); Isabelle McKenzie, Poquoson, VA (US)

(73) Assignee: Siemens VDO Automotive Inc., Chatham (CA)

( * ) Notice: Subject to any disclaimer, the term of this patent is extended or adjusted under 35 U.S.C. 154(b) by 140 days.

(21) Appl. No.: 10/452,840

(22) Filed: Jun. 2, 2003

(65) Prior Publication Data

US 2004/0004487 A1 Jan. 8, 2004

Related U.S. Application Data

(63) Continuation-in-part of application No. 10/150,903, filed on May 17, 2002, now Pat. No. 6,885,199.
(60) Provisional application No. 60/385,380, filed on Jun. 3, 2002, provisional application No. 60/341,022, filed on Oct. 30, 2001, provisional application No. 60/325,369, filed on Sep. 27, 2001, and provisional application No. 60/291,781, filed on May 17, 2001.

(51) Int. Cl.$^7$ .............................................. G01R 27/26
(52) U.S. Cl. ........................................ 324/686; 73/23.2
(58) Field of Search ........................................ 324/686

(56) References Cited

U.S. PATENT DOCUMENTS

| | | |
|---|---|---|
| 4,426,616 A | 1/1984 | Maier |
| 4,555,661 A | 11/1985 | Benson et al. |
| 4,915,084 A | 4/1990 | Gonze |
| 4,945,863 A | 8/1990 | Schmitz et al. |
| 4,971,015 A | 11/1990 | Gonze |
| 5,060,619 A | 10/1991 | Sakurai et al. |
| 5,089,703 A | 2/1992 | Schoen et al. |
| 5,103,184 A | 4/1992 | Kapsokavathis et al. |
| 5,119,671 A | 6/1992 | Kopera |
| 5,134,381 A | 7/1992 | Schmitz et al. |
| 5,216,409 A | 6/1993 | Ament et al. |
| 5,230,322 A | 7/1993 | Curran et al. |
| 5,231,358 A | 7/1993 | Kapsokavathis et al. |
| 5,255,656 A | 10/1993 | Rader et al. |
| 5,301,542 A | 4/1994 | Meitzler et al. |
| 5,361,035 A | 11/1994 | Meitzler et al. |
| 5,367,264 A | 11/1994 | Brabetz |
| 5,416,425 A | 5/1995 | Mouaici |
| 5,435,170 A * | 7/1995 | Voelker et al. ............. 73/53.05 |
| 5,493,897 A * | 2/1996 | Nomura et al. .............. 73/23.2 |
| 5,503,004 A | 4/1996 | Agar |
| 5,594,163 A | 1/1997 | Suzuki |
| 5,717,339 A | 2/1998 | Murphy et al. |
| 5,945,831 A | 8/1999 | Sargent et al. |

FOREIGN PATENT DOCUMENTS

| | | | | |
|---|---|---|---|---|
| DE | 199 38 790 A 1 | 2/2001 | | |
| GB | 2 210 459 A | 6/1989 | | |
| JP | 01163607 A | * 6/1989 | ............ | G01C/9/06 |

* cited by examiner

*Primary Examiner*—Charles H. Nolan, Jr.

(57) ABSTRACT

A sensor (20) includes a single capacitor (30) that operates in two different modes to obtain capacitance and conductance information when a mixture flows between the electrodes (32, 34) of the capacitor. Two different oscillators (180, 182) are selectively used to obtain the conductance and capacitance information. In a disclosed embodiment, a capacitor includes an outer electrode (32) that is received around an inner electrode (34) such that there is spacing between the electrodes through which the mixture flows. The mixture acts as a dielectric of the capacitor allowing the conductance and capacitance measurements to be made. A glass member (36) seals off the spacing between the electrodes and provides physical support to position the inner electrode to keep the electrodes electrically isolated.

16 Claims, 5 Drawing Sheets

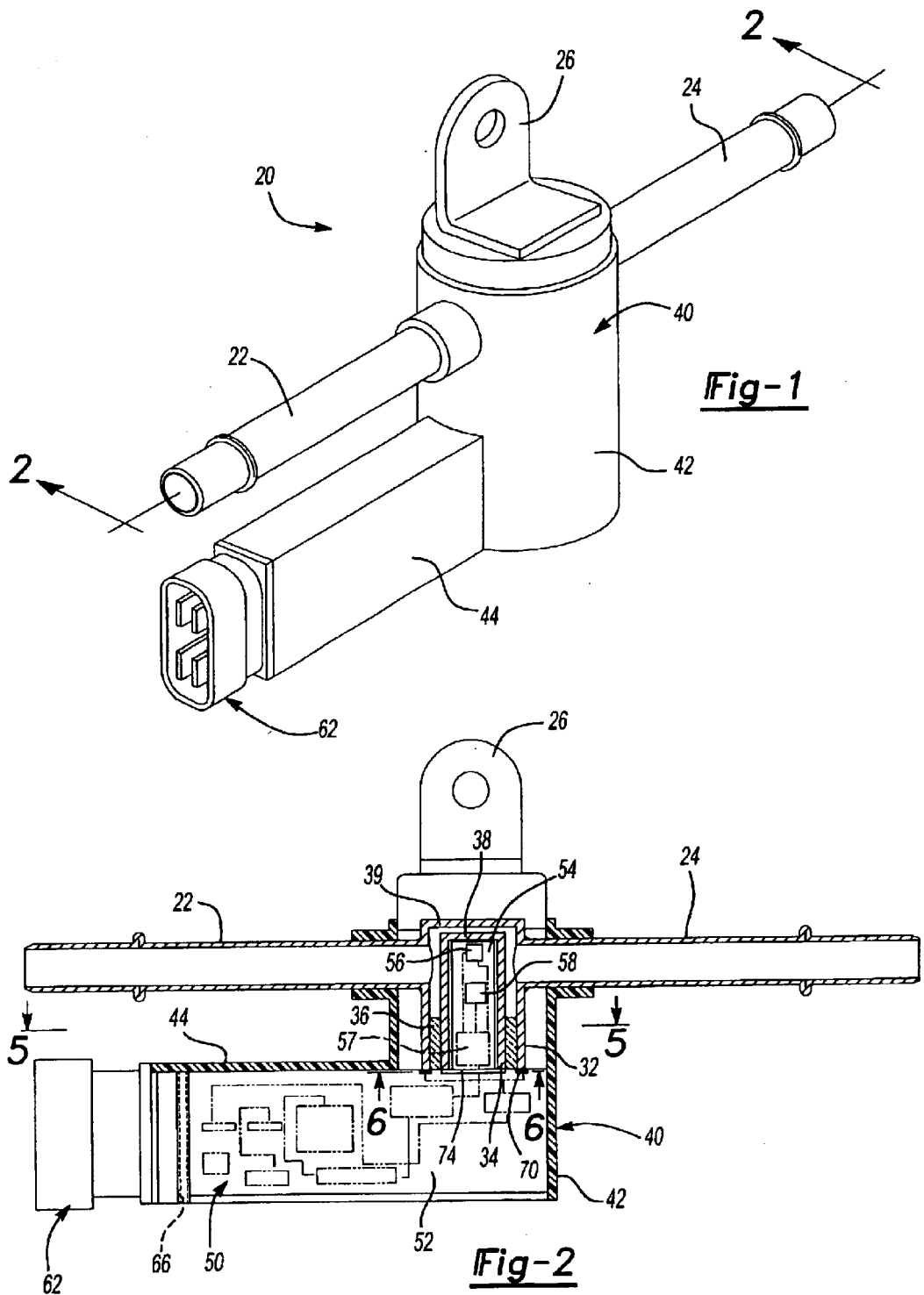

FUEL SENSOR

CROSS REFERENCE TO RELATED APPLICATIONS

This application claims priority to U.S. Provisional Application No. 60/385,380, which was filed on 3 Jun. 2002. This application is a continuation-in-part of U.S. Ser. No. 10/150,903, which was filed on 17 May 2002, which claims priority to U.S. Provisional Application Nos. 60/291,781, which was filed on 17 May 2001; 60/325,369, which was filed on 27 Sep. 2001; and 60/341,022, which was filed on 30 Oct. 2001.

BACKGROUND OF THE INVENTION

1. Technical Field

This invention generally relates to fluid content sensors. More particularly, this invention relates to a sensor arrangement having a single capacitor that is used in two different modes to determine desired characteristics of a fuel mixture, for example.

2. Description of the Prior Art

A variety of sensors for determining fluid contents are known. Fuel sensors, for example, typically are used to determine the content of a fuel mixture within a fuel system of a vehicle. Some sensors are capable of determining the content of the fuel mixture such as a ratio or proportion of alcohol to gasoline within the fuel. Depending on the determined ratio, the ignition timing and fuel quantity supplied by fuel injectors may be adjusted by a suitable fuel flow control system.

It is known that the relative permittivity and conductivity of substances or fluids differ from each other because of the different oxygen levels within each, for example. Accordingly, the relative contents of a fluid mixture of known components may be a well-defined function of the fluid's relative permittivity, temperature and conductivity.

Known sensors take advantage of these known characteristics and utilize the electrical properties of the fluid mixture contents to make a determination regarding concentrations, for example. Sample patents in this field of endeavor that are directed toward fuel systems include U.S. Pat. Nos. 4,945,863 and 5,367,264. Each of these patents show approaches to providing a fuel sensor that utilizes the electrical properties of the fluid for making fuel content determinations.

While the current approaches have proven satisfactory, those skilled in the art are always striving to make improvements. For example, packaging constraints on vehicle systems continuously cause an emphasis to be placed upon minimizing the size of components and maximizing the convenience of integrating them into vehicle systems. Additionally, cost savings are always a concern to automotive suppliers.

This invention addresses the need for providing an economical and convenient approach to measuring properties of a fuel.

SUMMARY OF THE INVENTION

In general terms this invention is a sensor that utilizes a single capacitor operated in two different modes for determining the conductivity and permittivity of a mixture to provide information regarding the contents of the mixture.

The capacitor of the sensor in one embodiment has a first, generally cylindrical electrode that is coaxially aligned with the other electrode. A glass seal electronically isolates the electrodes. In one example, the glass seal provides physical support to maintain the inner electrode in the proper position relative to the outer electrode. The mixture flows between the electrodes so that the appropriate conductivity and permittivity information can be determined. The capacitor effectively operates in two different modes (using two different oscillators in one example) so that the permittivity and conductivity measurements are made.

In one example, the outer electrode is connected directly to the fuel lines of a portion of the vehicle fuel supply system. In one particular example, the outer electrode is directly connected with portions of a fuel rail. A plastic housing is molded over the outer electrode and an associated portion of the fuel supply system. The housing includes a portion that supports a printed circuit board that includes electronics for operating the sensor. In one example, the printed circuit board is oriented at least partially perpendicular to the axes of the capacitor electrodes.

The various features and advantages of this invention will become apparent to those skilled in the art from the following detailed description of the currently preferred embodiment. The drawings that accompany the detailed description can be briefly described as follows.

BRIEF DESCRIPTION OF THE DRAWINGS

FIG. 1 schematically illustrates an example sensor designed according to this invention in perspective.

FIG. 2 is a cross-sectional view taken along the lines 2—2 in FIG. 1.

DETAILED DESCRIPTION OF THE PREFERRED EMBODIMENTS

FIG. 1 schematically shows a sensor 20 designed according to this invention. In this example, the sensor 20 is integrally incorporated into part of a fuel supply system for a vehicle. Supply tubing 22 and 24 are part of a fuel rail in one example. A connector 26 facilitates securing the example device in a selected position on a vehicle.

Figure 3:
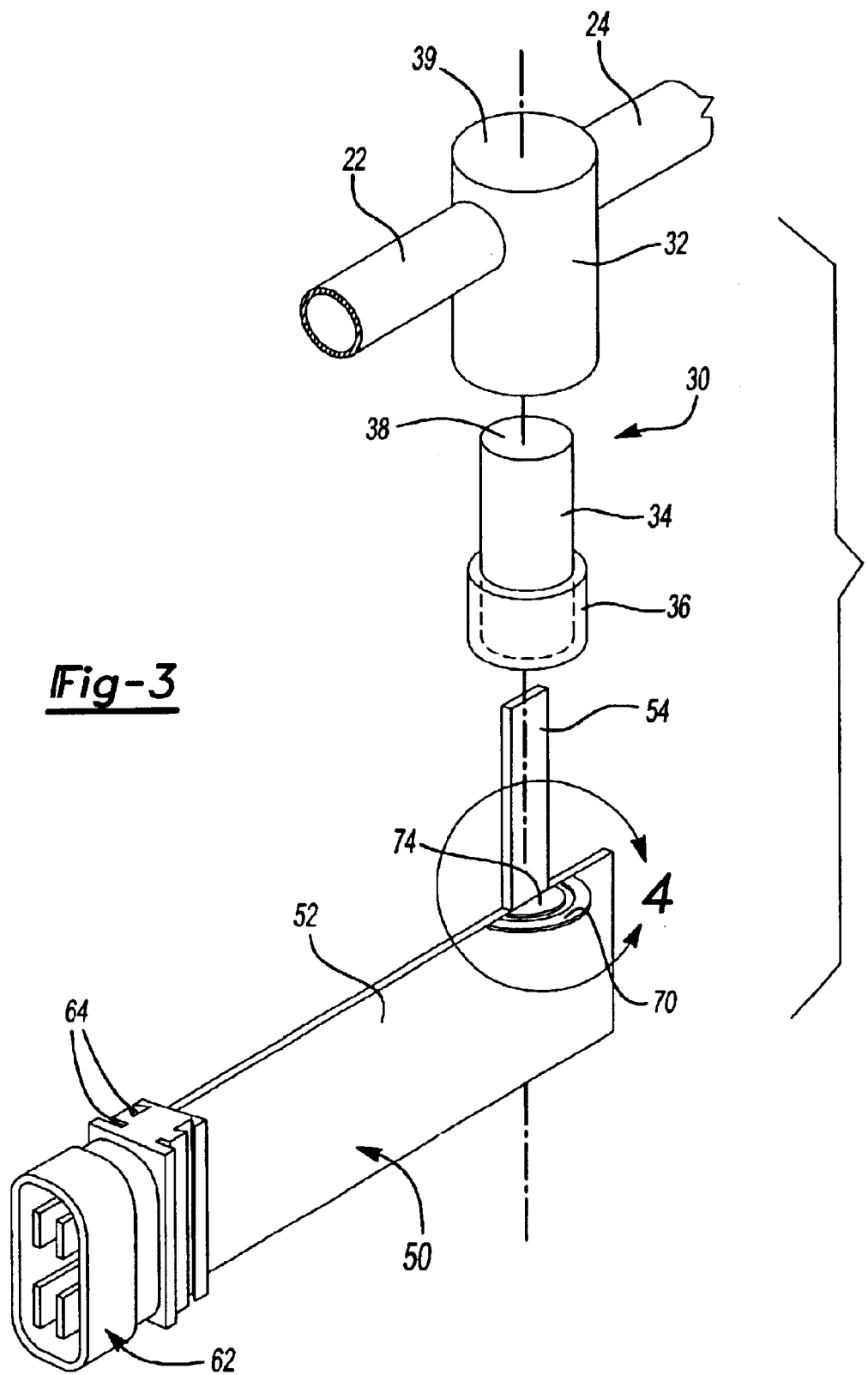
FIG. 3 is a partially exploded, schematic illustration of selected components of the embodiment of FIG. 1.

FIGS. 2 and 3 more specifically show selected components of the sensor embodiment of FIG. 1. The sensor 20 includes a single capacitor 30 having an outer electrode 32 and an inner electrode 34. In one example, the outer electrode is the cathode of the capacitor 30 and the inner electrode is the anode. A glass member 36 physically supports the inner electrode 38 within the outer electrode 32 and maintains the inner electrode 34 in an appropriate position so that the two electrodes remain electrically isolated.

In one example, the electrode 32 is brazed directly to the conduits 22 and 24. The fuel mixture flowing through the conduits 22 and 24 flows through the interior of the outer electrode 32 around the exterior of the inner electrode 34 such that the fluid acts as the dielectric of the capacitor.

The example glass member 36 operates to fluidly seal off one end of the chamber within the outer electrode 32. The inner electrode 34 includes a closed end 38 and the outer electrode 32 has a closed end 39. The outer electrode 32, together with the supply conduits 22 and 24 and the glass seal member 36 form a chamber between the electrodes through which the fluid mixture flows such that the contents of the mixture can be determined using the sensor 30.

In one example, the glass seal member 36 is preformed as a cylindrical ring. The glass seal 36 is placed between the electrodes 32 and 34 of the sensor capacitor 30. Heat is applied to at least partially melt the glass to establish a seal between the electrodes 32 and 34. In one example, the preformed cylindrical ring and the electrodes are passed through a furnace to achieve the appropriate heat level and sealing properties.

In one example, the material used for the glass seal member 36 is a known compressive glass. In one example, the outer electrode material has a higher thermal coefficient than that of the inner electrode. Accordingly, the glass seal member is compressed during the heating process. One supplier of such a compressive glass material is OSRAM.

The glass seal 36 not only provides a fluid seal at one end of the chamber between the two electrodes but also provides physical support to position the inner electrode 34 within the interior of the outer electrode 32 so that there is appropriate physical spacing between them to maintain electrical isolation between the electrodes. Accordingly, the glass seal 36 in the example embodiment has three functions; providing a fluid seal, providing physical support to the inner electrode to maintain the inner electrode in a desired position within the outer electrode and providing electrical insulation between the electrodes 32 and 34.

As best appreciated from FIGS. 1 and 2, the example embodiment includes a plastic housing 40 having a generally cylindrical portion 42 and a rectangular portion 44. The housing 40 in one example is overmolded onto the assembled electrodes and the fluid conduits 22 and 24. The cylindrical portion 42 maintains a protective housing around the electronics of the capacitor 30 of the sensor 20. The cylindrical portion 42 and the rectangular portion 44 provide support for electronics that are at least partially maintained within the housing 40 and which provide the ability to obtain mixture content information using the capacitor 30 of the sensor 20.

In the illustrated example, the electronics for operating the sensor 20 are supported on a printed circuit board substrate 50. In this example, a first portion 52 of the board substrate 50 is oriented generally perpendicular to a second portion 54, which is smaller than the first portion 52. In this example, the second portion 54 extends into the interior of the inner electrode 34.

In this example, the circuit board substrate second portion 54 supports a temperature sensor 56 such as a thermistor and two oscillators 57 and 58 that operate the capacitor 30 in the two different modes (permittivity and conductivity measurements) to make the mixture content determination. Placing the oscillators inside the electrodes isolates them from electromagnetic interference that might otherwise hinder their performance. A further discussion of example electronics suitable for use with a sensor designed according to this invention is provided below.

In the illustrated example, the circuit board substrate 50 preloaded with appropriate electronics is inserted into the housing 40 (from beneath in FIGS. 1 and 2). One end of the first portion 52 of the circuit board 50 is received within a slot 60 formed on the interior of the cylindrical portion 42 of the housing 40. An electrical connector portion 62 facilitates making a connection with other electronics that receive the information gathered using the sensor 20. The connector portion 62 in the illustrated example includes slots 64 (best seen in FIG. 3) that cooperate with extensions 66 on the housing portion 44 to maintain the electronics supported by the board 50 within the housing 40 in a desired position.

Figure 4:
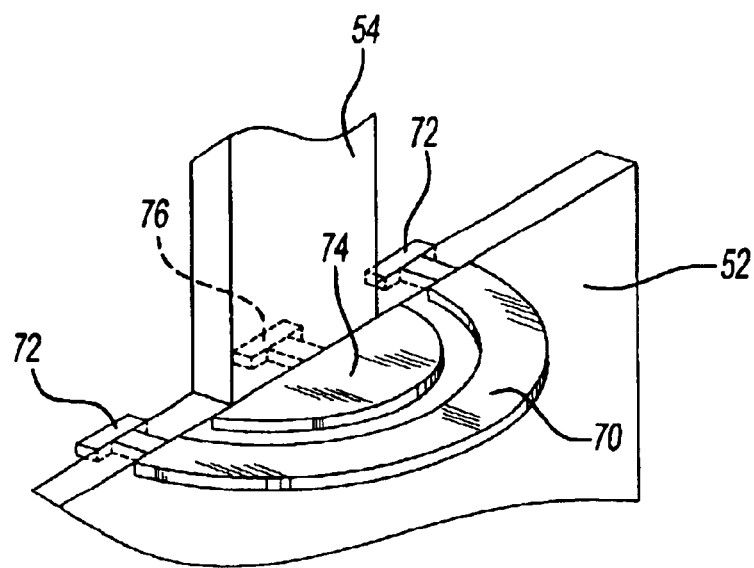
FIG. 4 is a schematic, enlarged view of the circled portion of FIG. 3.
Figure 5:
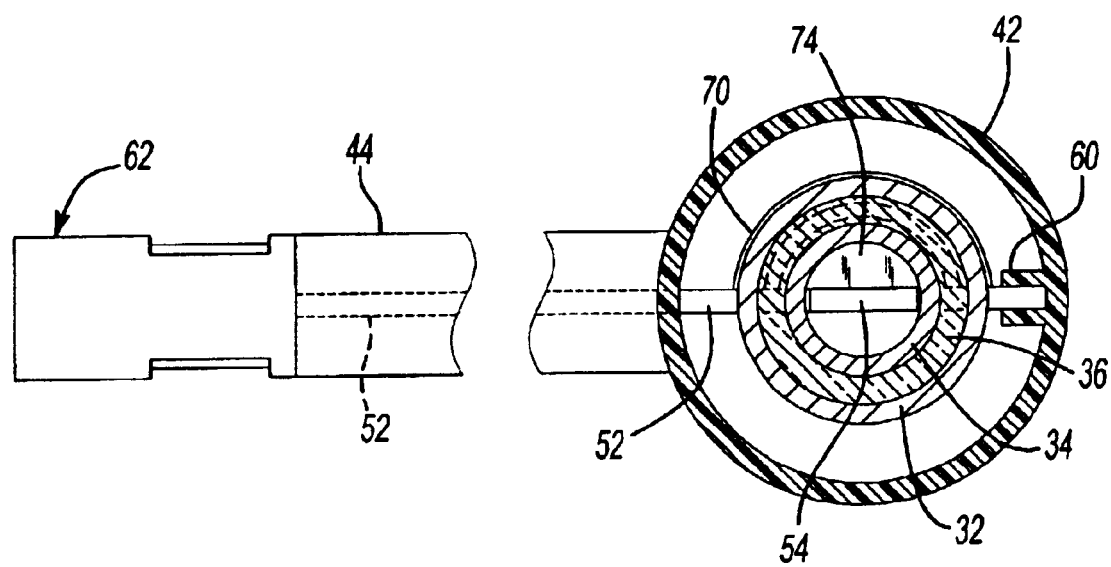
FIG. 5 is a view taken along the lines 5—5 in FIG. 2.

One advantage of the inventive arrangement is that inserting the electronic circuit board 50 into the housing 40 also makes appropriate electrical connections between the electronics supported on the board 50 and the electrodes of the capacitor 30. As best appreciated from FIGS. 4 and 5, a first conductive member 70 is supported on the first portion 52 of the circuit board 50. Extensions 72 are heat staked in one example onto the board substrate 52. The extensions 72 facilitate making electrical connections (by soldering, for example) with other electronics supported on the circuit board substrate 50. When the circuit board 50 is inserted into the housing 40, the conductor member 70 makes electrical contact with one end of the outer electrode 32. This can best be appreciated from FIGS. 2 and 5.

Another electrical connector member 74 is supported on the first portion 52 of the circuit board 50, which is immediately adjacent the interface between the first portion 52 and the second portion 54 in the illustrated example. The second conductive member 74 makes electrical contact with the inner electrode 34 when the circuit board 50 is appropriately positioned within the housing 40. An extension 76 that secures the conductive member 74 to the circuit board 50 also facilitates making electrical connections with other electronics supported on the circuit board substrate 50.

In one example, the conductive members 70 and 74 comprise half washers. In one example, the conductive members are welded to the electrodes of the capacitor 30 after the printed circuit board 50 has been appropriately inserted into the housing 40. The conductive members 70 and 74 provide a single mechanical connection between the electrodes and the other electronics of the sensor 20.

Having a portion of the housing 44 extending perpendicular to the axis of the cylindrical portion 42 provides support for the first portion 52 of the printed circuit board 50. Having the first portion 52 oriented at least partially perpendicular to the axes of the electrodes of the capacitor 30 provides several advantages. One advantage is having a more compact design for meeting packaging requirements of various situations. Another advantage is that the potting process where a gel is placed within the housing 40 to support the sensor components becomes more efficient. With the design of the illustrated example, any bubbles can escape during the potting process. Further, the inventive arrangement provides for the ability to have an equal amount of potting gel on both sides of the printed circuit board 50, which decreases mechanical stress during temperature variation, for example.

Attention will now be turned to the electronics used to operate the example embodiment of the inventive sensor. The general principles of making capacitance and conductance measurements are known. As will become apparent, the inventive sensor uses conventional measurement principles but also includes novel features distinguishing the inventive arrangement from prior sensors.

Figure 6:
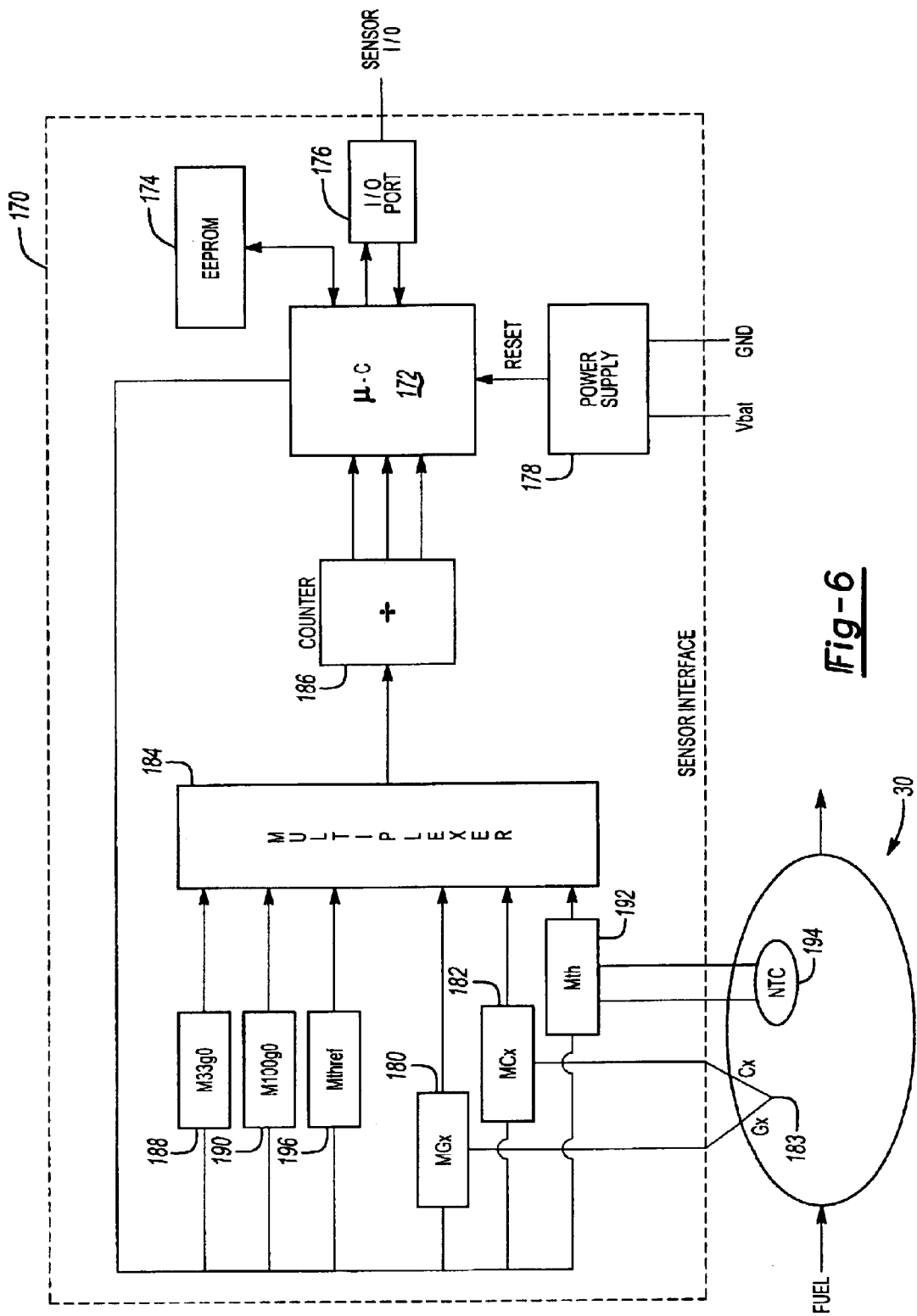
FIG. 6 schematically illustrates example electronics used to operate a sensor designed according to this invention.

FIG. 6 schematically illustrates the sensor capacitor 30 and electronics 170 for operating the sensor. A microprocessor 172 is suitably programmed to gather the capacity, temperature and conductivity information obtained by the sensor and to compare that information to data stored in the ROM of the controller 172 to make a mixture content determination. Calibration parameters of the sensor are stored in the EEPROM 174. In one example, the controller 172 ROM includes a look up table of a plurality of predetermined sensor values corresponding to specific known mixtures. The microprocessor 172 is programmed to utilize that information and provide an output through a conventional communication port 176 to be used by the mixture supply controller that is responsible for the amount of fuel supplied to a vehicle engine, for example. A conventional power supply 178 powers the microprocessor 172.

One unique feature of this invention is the use of a single capacitor 30 to make the conductivity and permittivity measurements of the mixture. Two different oscillators 180 and 182 are selectively coupled with the capacitor 30 to make the two separate determinations (i.e., conductivity and capacity). The inventive arrangement includes a single mechanical connection 183 between the capacitor 30 and the oscillators 180 and 182. Instead of switching the connection to the capacitor 30, the example implementation of this invention includes switching the oscillator (180 and 182) outputs. In such a case parasitic capacitance does not influence the capacity to measure.

The electronics 170 include a multiplexer 184 that receives the output of the oscillators 180 and 182. In one example, one of the oscillators operates in a MegaHertz range while the other operates in a KiloHertz range. Because of these relatively high frequencies, a counter 186, which acts as a divider, is provided between the multiplexer 184 and the microprocessor 172 so that the microprocessor is capable of handling the signal information from the oscillators. Although schematically shown as separate "components," the various portions of FIGS. 6 or 7 may be implemented using a suitably programmed microprocessor, for example. The illustrated divisions are applicable to the described example but this invention is not so-limited.

The inventive arrangement includes operating the oscillators 180 and 182 at different frequencies and independent from each other so that the capacitor 30 is used in two different modes, depending on which oscillator is activated.

To compensate for component drifting and aging, reference oscillators 188 and 190 are provided. In one example, the reference oscillator 188 is set to provide an indication of a methanol content at a lower end of an expected spectrum. The oscillator 190 is set to provide an indication corresponding to a methanol content at an opposite end of an expected spectrum. In one example the reference capacitor 188 corresponds to a ten percent methanol content while the reference capacitor 190 corresponds to a ninety percent methanol content. The reference oscillators preferably are selected to remain fixed so that they are not affected over the lifetime of the sensor assembly.

As mentioned, another factor used when making a mixture content determination is the temperature of the mixture. The illustrated example arrangement includes another oscillator 192 that is coupled with the thermistor 56 that obtains mixture temperature information. A reference oscillator 196 is chosen to provide calibration information to compensate for drift or aging of the oscillator 192 over time.

The use of oscillators in combination with capacitors for obtaining the necessary information regarding the mixture content are known. One advantageous difference of this invention is that a single capacitor 30 is used in two modes and only a single mechanical connection 183 between the capacitor 30 and the oscillators 180 and 182 simplifies the overall assembly and makes it more economical.

The microprocessor 172 preferably is programmed to selectively switch between the oscillators 180 and 182 to make the appropriate conductivity or capacity measurements. The example of FIG. 7 includes electronic switches 200 and 202 that are selectively operated by the microprocessor 172 to achieve the desired oscillator operation to obtain the desired measurement. Similarly, the microprocessor 172 controls electronic switches 204 and 206 to select either of the reference oscillators 188 and 190.

Figure 7:
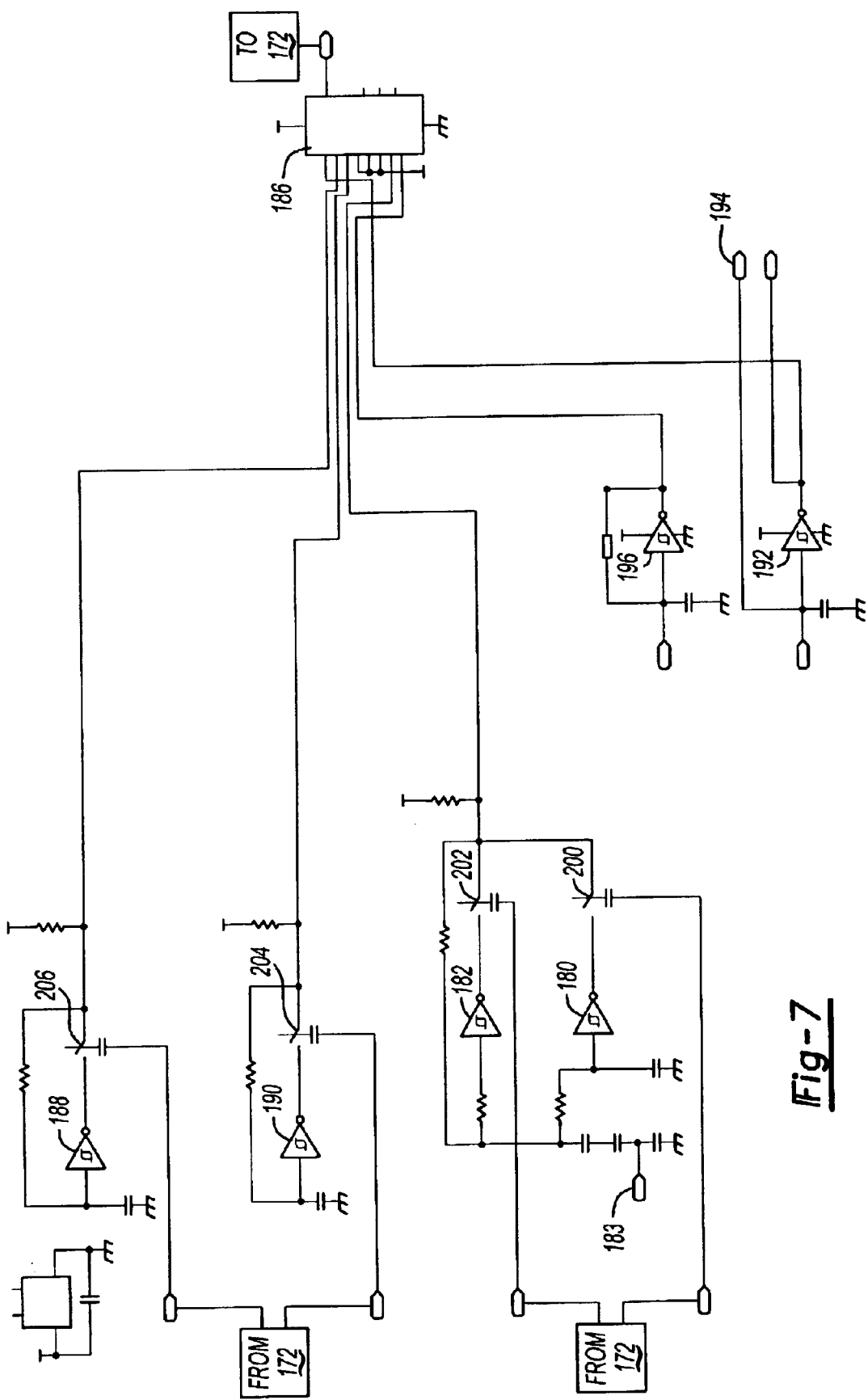
FIG. 7 schematically illustrates, in somewhat more detail, an example implementation of electronics for operating a sensor designed according to this invention.

The arrangement of electronics for operating a sensor designed according to this invention can take a variety of forms. The example of FIG. 7 is one particular implementation of the overall inventive strategy. Those skilled in the art who have the benefit of this description will be able to select from commercially available electronic components or to specially design hardware and software to meet the needs of their particular situation.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A sensor device, comprising:
    a single capacitor having a first generally cylindrical electrode and a second generally cylindrical electrode that is at least partially received within and coaxial with the first electrode;
    a glass member extending at least partially between the first and second electrodes to electrically isolate the electrodes and support the second electrode in a selected position relative to the first electrode; and
    a circuit board substrate that supports electronics, the substrate having a first portion that is aligned generally perpendicular to the electrode axes and a second portion that extends perpendicular to the first portion and wherein the second portion is received at least partially within the second electrode.

2. The device of claim 1, wherein the first electrode is generally cylindrical having an open end and wherein the glass member is near the open end, the glass member fluidly sealing a space between the first and second electrodes.

3. The device of claim 2, wherein the first electrode is secured to at least one conduit of a vehicle fuel supply such that the fuel flows inside of the first electrode and between the first and second electrodes.

4. The device of claim 1, including two oscillators supported on the substrate second portion.

5. The device of claim 1, including a first electrically conductive connector member and a second electrically conductive connector member supported by the substrate, the conductive members making electrical contact with the first and second electrodes, respectively, when the second portion is received at least partially within the second electrode.

6. The device of claim 5, wherein the electrically conductive connectors are welded to the respective electrodes.

7. A sensor device, comprising:
    a single capacitor having a first generally cylindrical electrode and a second generally cylindrical electrode that is at least partially received within and coaxial with the first electrode;
    a glass member extending at least partially between the first and second electrodes to electrically isolate the electrodes and support the second electrode in a selected position relative to the first electrode;

a circuit board substrate that supports electronics, the substrate having a first portion that is aligned generally perpendicular to the electrode axes; and a plastic housing molded over the first electrode and having a portion that receives and supports at least the first portion of the substrate.

8. The device of claim 7, including a first electrically conductive connector member and a second electrically conductive connector member supported by the substrate, the conductive members making electrical contact with the first and second electrodes, respectively, when the substrate is received in the housing.

9. The device of claim 7, wherein the housing includes a generally cylindrical portion that is received over the first electrode and a second generally rectangular portion extending generally perpendicularly away from an axis of the generally cylindrical portion.

10. The device of claim 1, wherein the glass member seals off at least one end of a fluid chamber between the first and second electrodes such that fluid within the chamber operates as a dielectric of the capacitor.

11. The device of claim 1, including a plastic housing that is molded over at least a portion of the first electrode.

12. A sensor device, comprising:

a single capacitor having a first electrode and a second electrode that is at least partially received within the first electrode, wherein one of the first electrode or the second electrode has a thermal coefficient that is higher than the other electrode; and a glass member extending at least partially between the first and second electrodes to electrically isolate the electrodes and support the second electrode in a selected position relative to the first electrode.

13. A method of assembling a fuel sensor, comprising the steps of:

arranging two electrodes such that spacing exists between the electrodes through which fluid may flow by placing one of the electrodes at least partially within the other electrode;

placing a glass member between the two electrodes by placing the glass member over the one electrode before inserting the one electrode into the other electrode; and subsequently heating the electrodes and the glass member to seal an interface between the glass member and each of the electrodes, to secure the glass member to each of the electrodes and to maintain the spacing between the electrodes.

14. The method of claim 13, wherein the electrodes have different thermal coefficients and including compressing the glass member between the electrodes.

15. The method of claim 13, including subsequently molding a plastic housing at least partially over one of the electrodes.

16. A method of assembling a fuel sensor, comprising the steps of:

arranging two electrodes such that spacing exists between the electrodes through which fluid may flow;

placing a glass member between the two electrodes;

securing the glass member to each of the electrodes to thereby maintain the spacing between the electrodes; and subsequently molding a plastic housing at least partially over one of the electrodes.

\* \* \* \* \*